(12) United States Patent
Ikehara et al.

(10) Patent No.: US 7,541,025 B2
(45) Date of Patent: Jun. 2, 2009

(54) TREATMENT OF MALIGNANT TUMOR

(75) Inventors: Susumu Ikehara, Osaka (JP); Yasushi Adachi, Moriguchi (JP); Yasuhiro Suzuki, Osaka (JP)

(73) Assignee: Jimro Co., Ltd., Gunma (JP)

( * ) Notice: Subject to any disclaimer, the term of this patent is extended or adjusted under 35 U.S.C. 154(b) by 704 days.

(21) Appl. No.: 10/786,094

(22) Filed: Feb. 26, 2004

(65) Prior Publication Data

US 2004/0166103 A1 Aug. 26, 2004

(30) Foreign Application Priority Data

Feb. 26, 2003 (JP) ............................. 2003-049198

(51) Int. Cl.
- *A61K 35/12* (2006.01)
- *A61K 35/14* (2006.01)
- *C12N 5/06* (2006.01)
- *C12N 5/08* (2006.01)
- *A61N 5/10* (2006.01)

(52) U.S. Cl. ................... 424/93.7; 424/93.71; 424/423; 378/65; 607/88

(58) Field of Classification Search ....................... None
See application file for complete search history.

(56) References Cited

U.S. PATENT DOCUMENTS

| | | | | |
|---|---|---|---|---|
| 5,229,109 A | * | 7/1993 | Grimm et al. | ............... 424/85.2 |
| 5,514,364 A | | 5/1996 | Ildstad | |
| 6,383,481 B1 | * | 5/2002 | Ikehara et al. | ............... 424/93.1 |
| 6,558,662 B2 | * | 5/2003 | Sykes et al. | ................ 424/93.1 |

OTHER PUBLICATIONS

Dictionary of Immunology, 1985 Herbert et al, Ed.s, p. 8 "alloantigen".*
Ashkenasy (Stem Cells, 2002, vol. 20, pp. 86-93).*
Matthes-Martin et al (Bone Marrow Transplantation, 2000, vol. 26, pp. 377-382).*
Roush et al (Transfusion Medicine Reviews, 2002, vol. 16, pp. 161-176).*
abstract of Ballester et al (Blood, vol. 100, No. 11, abstract No. 5198).*
Kushida et al (Blood, 2001, vol. 97, pp. 3292-3299).*
Sherer and Shoenfeld (Bone Marrow Transplantation, 1998, vol. 22, pp. 873-881).*
Drobyski et al (Journal of Immunology, 2000, vol. 165, pp. 1634-1640).*
Yamamoto et al, *Blood*, 88(2):445-454 (1996).
Carella et al, *Bone Marrow Transplantation*, 25:345-350 (2000).
Di Nicola et al, *Blood*, 99(10):3838-3843.
Martino et al, *Blood*, 100(6):2243-2245 (2002).
Billiau et al, *Blood*, 100(5):1894-1902 (2002).

* cited by examiner

*Primary Examiner*—Karen A Canella
(74) *Attorney, Agent, or Firm*—Sughrue Mion, PLLC

(57) ABSTRACT

The invention provides a technology which utilizes donor lymphocyte infusion and by which malignant tumor can be treated without causing such an adverse effect as graft versus host disease. Thus, a method for the treatment of malignant tumor is provided which comprises performing, in a patient requiring such treatment, donor lymphocyte infusion for the graft versus tumor reaction-based treatment of tumor and then performing radiation treatment, infusion of lymphocytes derived from the host or a third party identical in HLA type to the host, and intra bone marrow-bone marrow transplantation using bone marrow cells derived from the host or a third party identical in HLA type to the host, for the prevention and treatment of the graft versus host disease induced by the donor lymphocyte infusion.

11 Claims, 2 Drawing Sheets

TREATMENT OF MALIGNANT TUMOR

FIELD OF THE INVENTION

This invention relates to a method for the treatment of various kinds of malignant tumor, inclusive of solid cancer and sarcoma.

DESCRIPTION OF THE RELATED ART

A therapy for the prevention of recurrence of hematopoietic tumor after allogenic bone marrow transplantatipon which therapy comprises transfusing lymphocytes from the same donor has been established in the field of hematopoietic tumors, such as leukemia [donor lymphocyte infusion (DLI) or donor leukocyte transfusion (DLT); hereinafter this therapy is referred to as "DLI"; cf. e.g. Shintaro Shiobara: "DLI no Tekio to Hoho (Indication and methods of DLI)", Ketsueki Shuyoka (Hematology & Oncology), 42(2):151-157, 2001].

The principle of DLI consists in utilizing the attacking action of donor lymphocytes (immunocompetent cells, mainly T cells) transfused on leukemic cells that have recurrently begun to proliferate (i.e. graft versus leukemia reaction, hereinafter referred to as "GVLR").

However, donor lymphocytes not only attack the above-mentioned leukemic cells but also recognize the patient (recipient) himself or herself as a foreign matter, attacking, damaging and killing normal tissues, for example liver, digestive tract, and skin, of the patient and thus causing the graft versus host reaction (GVHR) or graft versus host disease (GVHD). (Such reaction or disease is hereinafter referred to as "GVHD".)

DLI has been proposed as a method of treatment not only of leukemia but also of solid cancers and so forth. In this case, the graft versus tumor reaction (hereinafter referred to as "GVTR") can be expected to produce a curative effect. However, in this therapy, too, the onset of GVHD is a serious harmful effect. Since no method has yet been established for the prevention or treatment of GVHD, the clinical application of DLI entails a risk to the patient, hence the practicability thereof is questionable.

As discussed above, leukemia, malignant tumors and the like may be completely cured by DLI, which utilizes GVLR or GVTR, when it is repeated frequently. Such frequent repetition of DLI results in increases in incidence and severity of GVHD as an adverse effect. Therefore, it is still difficult to attain complete cure of malignant tumor by the clinical practice of DLI.

Thus, it is earnestly demanded in the relevant field of art that a novel technology by which the occurrence of GVHD can be prevented or, after occurrence thereof, GVHD can be dealt with be developed.

The primary object of this invention is to establish a therapy of malignant tumor for attaining complete cure. More specifically, the invention has for its object to establish a technology according to which GVHD induced as an adverse effect in that technology of treating malignant tumor which utilizes the technique of DLI so far proposed in the art can be suppressed or avoided (prevented and treated).

SUMMARY OF THE INVENTION

The inventors have so far made investigations concerning the technology of attaining immunological tolerance, which is effective in the field of bone marrow transplantation and organ transplantation, among others. In the course thereof, they found that when donor-derived bone marrow cells are directly administered into the bone marrow of a recipient (intra bone marrow-bone marrow transplantation, hereinafter referred to as "IBM-BMT") after irradiation as a pretreatment, the hematopoietic system of the recipient can be replaced with that of the donor while avoiding any insufficient take of transplant cells or rejection reaction thereto and without GVHD, and thus long-term take and retention of the transplant bone marrow or transplant organ can be attempted. Based on this finding, an invention has been established (cf. Japanese Unexamined Patent Publication No. 2001-172188).

Paying their attention to the fact that GVHD will not manifest itself in this IBM-BMT, the inventors assumed that if this technology could be utilized for suppressing or avoiding GVHD as an adverse effect induced in the treatment of malignant tumor by means of DLI, a therapy for complete cure of malignant tumor would be established. Further intensive investigations made by the inventors based on this idea have now led to achievement of the present invention. The subject matter of the invention is shown below in Items 1 to 14.

1. A method for the treatment of malignant tumor which comprises performing DLI in a patient requiring such treatment and then performing radiation treatment (irradiation), infusion of lymphocytes derived from the host, i.e. the patient, or a third party identical in the type of HLA (human lymphocyte antigens) to the host (such infusion is hereinafter referred to as "HLI"), and intra bone marrow-bone marrow transplantation (IBM-BMT) using bone marrow cells derived from the host or a third party identical in HLA type to the host (hereinafter collectively referred to also as "host type bone marrow cells").

2. The method for the treatment of malignant tumor as defined above under Item 1, wherein the DLI is for GVTR-based tumor treatment, and the radiation treatment, HLI and intra bone marrow-bone marrow transplantation (IBM-BMT) using host type bone marrow cells are for the prevention and treatment of DLI-induced GVHD.

3. The method for the treatment of malignant tumor as defined above under Item 1, wherein a further radiation treatment is performed prior to DLI.

4. The method for the treatment of malignant tumor as defined above under Item 1, wherein the DLI is performed in the manner of intravenous administration of an effective amount of donor-derived peripheral blood mononuclear cells (hereinafter referred to as "PBMNCs").

5. The method for the treatment of malignant tumor as defined above under Item 1, wherein the radiation treatment following DLI is performed in the manner of total body irradiation (hereinafter referred to as "TBI") at a dose of 3-4 Gy.

6. The method for the treatment of malignant tumor as defined above under Item 1, wherein the HLI is performed in the manner of intravenous administration of an effective amount of PBMNCs derived from the host or a third party identical in HLA type to the host.

7. The method for the treatment of malignant tumor as defined above under Item 1, wherein the bone marrow cells are whole bone marrow cells (hereinafter referred to as "WBMCs") derived from the host or a third party identical in HLA type to the host.

8. The method for the treatment of malignant tumor as defined above under Item 1, wherein the bone marrow cells are WBMCs obtained by inserting a bone marrow puncture needle into one end of the long bone of the host or a third party identical in HLA type to the host, causing an irrigating fluid to flow via the needle through the medullary cavity and recovering the irrigating fluid containing bone marrow cells from a perforation provided at the other end of the long bone.

9. The method for the treatment of malignant tumor as defined above under Item 1, wherein the intra bone marrow-bone marrow transplantation (IBM-BMT) is performed in the manner of administration, into a long bone, of an effective amount of WBMCs derived from the host or a third party identical in HLA type to the host.

10. A method for the treatment of malignant tumor which comprises performing DLI for GVTR-based tumor treatment in a patient requiring such treatment and then performing radiation treatment and intravenous administration of peripheral blood stem cells derived from the host or a third party identical in HLA type to the host (such cells are hereinafter referred to as "PBSCs" and such administration is hereinafter referred to as "PBSCT") for the prevention and treatment of GVHD caused by said DLI.

11. The method for the treatment of malignant tumor as defined above under Item 1, wherein the malignant tumor is selected from among leukemia, malignant lymphoma, multiple myeloma, sarcoma, melanoma, brain tumor, stomach cancer, tongue cancer, esophageal carcinoma, colorectal cancer, liver cancer, gallbladder carcinoma, pancreatic carcinoma, renal carcinoma, bladder cancer, nasopharyngeal cancer, laryngeal cancer, skin cancer, mammary cancer, testicular cancer, ovarian cancer, uterus carcinoma, and lung cancer.

12. A pharmacological composition for use in the malignant tumor treatment method as defined above under Item 1 which comprises (1) a composition containing donor-derived PBMNCs, (2) a composition containing PBMNCs derived from the host or a third party identical in HLA type to the host and (3) a composition containing WBMCs derived from the host or a third party identical in HLA type to the host.

13. A method for the prevention and treatment of DLI-induced GVHD which comprises performing, in a patient requiring the prevention and treatment of GVHD, radiation treatment, HLI and intra bone marrow-bone marrow transplantation (IBM-BMT) using host type bone marrow cells.

14. A pharmacological composition for use in the method for the prevention and treatment of DLI-induced GVHD as defined above under Item 13 which comprises (1) a composition containing PBMNCs derived from the host or a third party identical in HLA type to the host and (2) a composition containing WBMCs derived from the host or a third party identical in HLA type to the host.

The most characteristic feature of the malignant tumor treatment method according to the invention is that malignant tumor can be completely cured while fully preventing or avoiding the onset of GVHD as an adverse effect, which is the most important drawback of the technique of DLI so far proposed.

The malignant tumor which can be completely cured by the method of this invention includes malignant tumors of the hematopoietic cells, such as leukemia, malignant lymphoma, and multiple myeloma; malignant tumors other than those of the hematopoietic cells, for example melanoma, sarcoma, and brain tumor; and all organ cancers (solid cancers) such as stomach cancer, tongue cancer, esophageal carcinoma, colorectal cancer, liver cancer, gallbladder carcinoma, pancreatic carcinoma, renal carcinoma, bladder cancer, nasopharyngeal cancer, laryngeal cancer, skin cancer, mammary cancer, testicular cancer, ovarian cancer, uterus carcinoma, and lung cancer.

The reason why various sorts of tumors can be completely cured in that manner by the method of the invention is presumably as follows. In the method of the invention, DLI is first performed in a patient with malignant tumor to replace the hematopoietic system of the patient with that of a donor. The thus-constructed donor-derived hematopoietic system (mainly T lymphocytes) attacks the tumor cells of the patient in the manner of GVTR, damaging and killing them and producing a curative effect on the tumor. On the other hand, the donor-derived hematopoietic system regards normal tissues of the patient as a foreign matter and causes GVHD to eliminate the same. In accordance with the invention, however, after DLI, radiation treatment, HLI, and IBM-BMT using host type bone marrow cells are carried out, whereby the onset of GVHD can be prevented or the disease can be treated. More specifically, those lymphocytes which are causative of GVHD are killed by irradiation at a low dose of 3-4 Gy. Further, a host versus graft reaction (hereinafter referred to as "HVGR") is caused by replacing the donor-derived hematopoietic system again with the hematopoietic system of the patient (reconstruction of the latter system) through HLI. In addition, the environment for the above-mentioned reconstruction of the hematopoietic system of the patient is improved or adjusted by IBM-BMT to thereby facilitate the reconstruction and render it sufficient and at the same time completely inhibit the function of the remaining donor-derived hematopoietic system (mainly T cells). In other words, said IBM-BMT efficiently supplements the host's bone marrow with stromal cells of the host. The cells proliferate and differentiate, and cytokines secreted therefrom and capable of inhibiting the function of T cells prevent the onset of GVHD and promote HVGR. The method of the invention utilizes such mechanisms of action, hence can be termed "revenge therapy".

The inventors also found that when intravenous administration of host-derived PBSCs is performed in lieu of the above-mentioned HLI and IBM-BMT using host type bone marrow cells, the PBSCs can perform the same function as that of PBMNCs and of WBMCs and, accordingly, the onset of GVHD is suppressed and the HVGR is promoted.

Anyhow, the method of the invention makes it possible to completely inhibit or avoid GVHD as an adverse effect possibly induced by DLI and completely cure various sorts of malignant tumor by frequently repeating DLI by which malignant tumor can be completely erased.

BRIEF DESCRIPTION OF THE SEVELAL VIEWS OF THE DRAWINGS

DETAILED DESCRIPTION OF THE INVENTION

Figure 1:
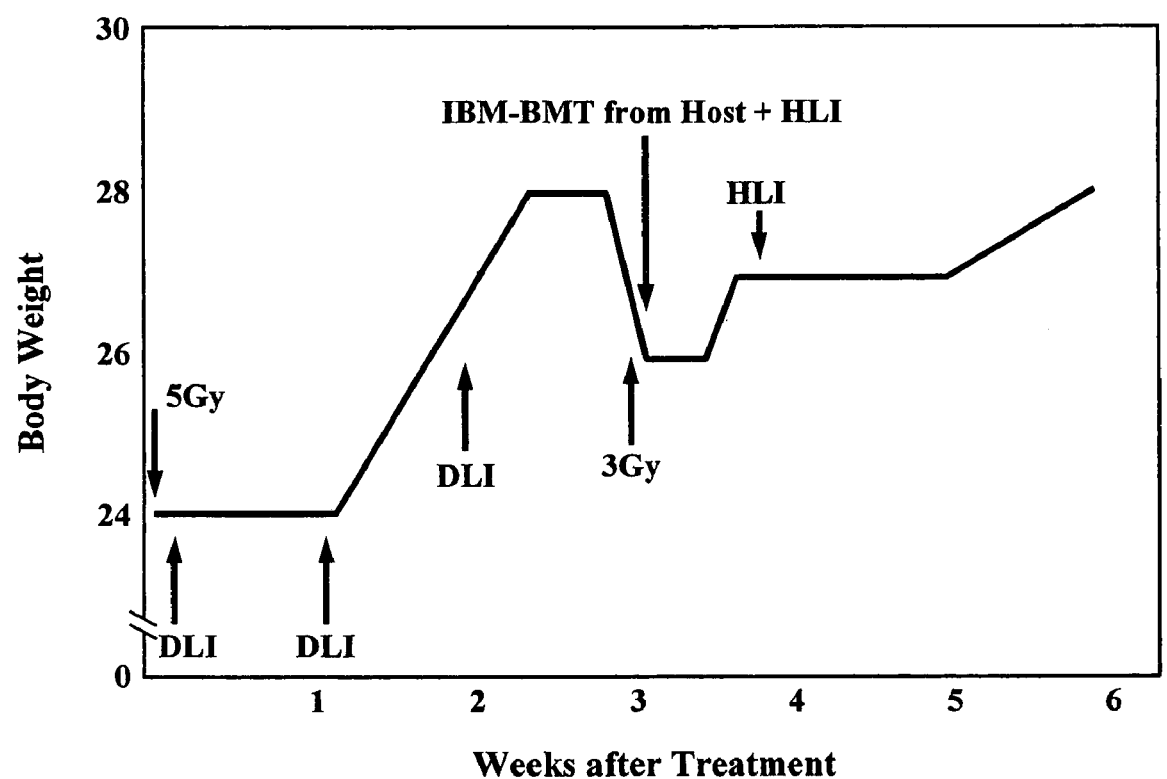
FIG. 1 is a graphic representation of the therapeutic effects on a malignant tumor (body weight changes in test animals) as produced in accordance with the invention.

The procedures (steps) to be employed in carrying out the method of the invention are described one by one in detail in the following.

(1) DLI

The DLI employed in accordance with the invention can be performed basically in the same manner as the conventional DLI in recurrence therapy for leukemic cells (cf. Shintaro Shiobara, Hematology & Oncology, 42(2):151-157, 2001).

The donor is preferably a normal subject. Further, the donor is preferably allogeneic to the patient (host), to whom the method of the invention is to be applied, but not in agreement in histocompatibility antigens (HLA) with the host. Thus, for producing a better curative effect, one who shows strong interactivity in the mixed lymphocyte reaction (MLR) with lymphocytes of the host, as revealed by preliminary testing, is preferably selected as the donor.

The donor lymphocytes to be used in DLI are selected from among PBMNCs derived the allogeneic mentioned above. The collection and preparation of PBMNCs can be performed in the conventional manner.

In the practice of the invention, DLI is carried out in the manner of intravenous infusion of PBMNCs. In particular, those PBMNC preparations obtained by the ordinary method contain T cells at a level of about 50% or higher and therefore readily cause GVTR and make it possible to carry out HVGR effectively, hence are preferred.

The amount of PBMNCs to be transfused and the frequency of transfusions can be appropriately determined depending on the condition (age, sex, body weight) of the patient (host) and the severity of disease, among others, without any particular restriction. Generally, the amount is usually selected within the range of about $1\times10^7$ to $1\times10^8$ cells/kg per shot. The frequency of transfusions and the interval thereof may be such that the desired GVTR-based curative effect on malignant tumor can be produced. Generally, at least two, usually about 3-5, transfusions are performed usually at intervals of 4-7 days.

For producing the curative effect of this DLI on malignant tumor with more certainty, the method of the invention may further comprise subjecting the host to irradiation treatment as a pretreatment prior to DLI. This irradiation treatment has for its object to destroy as much lymphatic system and hematopoietic cells of the host as possible. Generally, total body irradiation (TBI) at a dose of at most about 5 Gy is sufficient. This TBI is judiciously performed on the same day (within 24 hours) as the day of DLI (first time).

(2) Irradiation

According to the method of the invention, after the above DLI (1), irradiation, HLI and IBM-BMT using host type bone marrow cells are carried out. These procedures are preformed for the prevention and treatment of DLI-induced GVHD (judged based, for example, on the host body weight loss as an index).

This post-DLI irradiation is preferably carried out within one week following DLI (last time), with the reduction in size of malignant tumor, host body weight loss as an adverse effect and diarrheal symptoms, for instance, as induced by the DLI performed, being taken as indicators. This irradiation is performed as a pretreatment for the reversion of the donor-derived hematopoietic system constructed (substituted) by the DLI performed again to the host-derived hematopoietic system, namely as a procedure for destroying the donor-derived hematopoietic system. Generally, it is performed in the manner of TBI at a dose of at most about 4 Gy, usually about 3-4 Gy, more preferably about 3 Gy.

(3) HLI

HLI is performed utilizing PBMNCs derived from the host or a third party identical in HLA type thereto. Here, the collection and preparation of PBMNCs can be carried out in the same manner as the collection and preparation of donor-derived PBMNCs as described above under (1).

Host-derived PBMNCs may be collected and prepared from the host in advance prior to the start of the cancer therapy according to the invention. In case the host is, for example, a leukemia patient, however, the possibility of leukemic cells being contained in the peripheral blood of the host is high. In such a case, PBMNCs derived from a third party (normal healthy subject) identical in HLA type to the host are utilized in lieu of host-derived PBMNCs. The occurrence or nonoccurrence of leukemic cells can be verified in the conventional manner by the polymerase chain reaction (hereinafter referred to as "PCR") or flow cytometry, for instance.

The HLI according to the invention is performed in the manner of intravenous administration (transfusion) of PBMNCs. The amount of the host type cells to be transfused and the frequency of transfusions can be appropriately determined depending on the condition (age, sex, body weight) of the patient (host) and the severity of disease, among others, without any particular restriction. Generally, the amount is selected within the range of about $1\times10^7$ to $1\times10^8$ cells/kg per shot. The frequency of transfusions may be such that the desired HVGR-due, GVHR-inhibiting effect can be produced. While one single transfusion may be sufficient to produce such effect in some instances, the HLI is preferably repeated about 2-3 times at intervals of 4-7 days. The HLI can be performed on the same day as the day of the preceding irradiation treatment, namely within 24 hours following the irradiation treatment.

(4) IBM-BMT

In accordance with the invention, IBM-BMT is carried out simultaneously with the HLI mentioned above under (3). The bone marrow cells to be utilized here are of host type, namely ones derived from the host or a third party (normal subject) identical in HLA to the host. Collection and preparation thereof can be made by any of the methods known in the art [cf. e.g. Blood, vol. 88, pp. 445-454 (1996); "Saibo-Men'eki Jikken Sosaho" (Selected Methods in Cellular Immunology) (Mishell, B. B., Shgi, S. M. (eds.), jointly translated into Japanese by Katsuyuki Imai, Susumu Kawaguchi and Takayuki Harada, published by Rikogaku Publishing Co., pages 3-12, 1982)].

Specific examples of the BMCs are WBMCs obtained from the iliac bone, for instance, in the conventional manner, for example by suction. When such a method is employed, peripheral blood-derived erythrocytes are preferably removed in advance, while the presence of T cells does not present any particular problem.

Most preferred as BMCs are BMCs obtained by the irrigation method established previously by the inventors (generally containing T cells at a level of at most about 6% and containing stromal cells; cf. Japanese Unexamined Patent Publication No. 2001-172188). Specifically, the irrigation method comprises inserting a bone marrow puncture needle into one end of the long bone of the host or a third party identical in HLA type to the host, allowing an irrigating fluid to flow via the needle through the medullary cavity and recovering the irrigating fluid containing BMCs from a perforation provided at the other end of the long bone. More specifically, as an example, a bone marrow puncture needle is inserted, under anesthesia, into the bone marrow at a proximal site of the lateral condyle of the femur (in the case of the humerus, at a distal site of the greater tubercle) perpendicularly to the axis thereof, one end of an extension tube is connected with the needle and the other end of the tube is placed in a culture flask with heparin-containing, phosphate-buffered saline (PBS) placed therein. Another bone marrow puncture needle is inserted into the bone marrow at a distal site of the greater trochanter of the femur (in the case of the humerus, at a proximal site of the lateral condyle) perpendicularly to the axis thereof, and connected with a PBS-containing syringe.

PBS is slowly extruded from the syringe into the medullary cavity to wash out the bone marrow, and the bone marrow-containing medium is recovered in the above-mentioned flask. In this manner, BMCs (WBMCs) with a very low peripheral blood (erythrocyte and T cell) content can be obtained.

In case the host is, for example, a leukemia patient in the practice of the invention, there is the possibility of leukemic cells being contained in BMCs of the host, like in the above-mentioned case of PBMNCs. In such a case, BMCs derived from a normal healthy person identical in HLA type to the host are utilized in lieu of the host-derived BMCs. The occurrence or nonoccurrence of leukemic cells can be judged in the same manner as described above under (3) for PBMNCs.

The intra-bone marrow administration (IBM-BMT) of the host type BMCs as prepared in the manner mentioned above can be performed by injection utilizing a needle inserted into the bone marrow in the long bone (of the tibia or the femur, for instance). Particulars thereof are as described later herein in the example section. This method is characterized in particular as being less invasive to the recipient.

The dose of BMCs to be transfused into the bone marrow may be at such as level at which GVHR can be prevented. More specifically, it may be generally about $1\times10^7$ to $5\times10^8$ cells/kg, preferably about $1\times10^8$ cells/kg.

(5) PBSCT

In accordance with the invention, it is also possible to perform intravenous administration (transfusion) of host type PBSCs in lieu of the HLI and IBM-BMT described above under (3) and (4). The PBSCs to be utilized here can be collected and prepared by a general method described in the literature, for example by the method described in "Zoketsu Kansaibo Ishoku Manual (Hematopoietic Stem Cell Transplantation Manual)", 1st edition, 2nd printing, published Apr. 20, 1996 by Nihon-Igakukan, pages 351-360. In collecting PBSCs, peripheral blood can be mobilized in advance in the conventional manner by administering a hematopoietic factor having a mobilizing effect, for example granulocyte-colony-stimulating factor (hereinafter referred to as "G-CSF") or cytosine-arabinoside (Ara C). In collecting PBSCs, a continuous blood component collector (e.g. blood cell separator) generally used in blood component donation, for instance, can be used. The PBSCs prepared are stored in a refrigerator at $-80°$ C. or in a liquid nitrogen bath, and thawed just prior to use under conditions at $37°$ C.

The procedure for transfusing PBSCs can be carried out in the same manner as the HLI described above under (3). The amount of PBSCs and the number of transfusions may be the same as in the case of PBMNCs transfusion described above under (3).

(6) Supplementary Treatment Procedures

By performing the procedures described above under (1) to (4) or the procedures described above under (1), (2) and (5) according to the method of the invention, it is possible to treat malignant tumor for complete cure. As a matter of course, however, it is preferred that the target malignant tumor be surgically excised as far as possible. Therefore, the method of the invention is preferably combined with such surgical excision. Further, chemotherapy, which uses an anticancer agent, and radiotherapy have so far been developed as means for treatment or diminution of malignant tumor and each has been considered as being effective to a certain extent. It is of course possible to carry out the method of the invention in combination with such chemotherapy and/or radiotherapy as means for diminishing malignant tumor. Furthermore, the method of the invention may also be combined with various techniques of antibody therapy, cytokine therapy, vaccine/gene therapy, biological response modifier therapy and the like that have already been proposed.

In accordance with the invention, it is possible to provide a made-to-order method for the treatment of malignant tumor which is best suited for each individual patient with malignant tumor.

As described hereinabove, the method of the invention has made it possible to completely cure malignant tumor without any substantial adverse effect, and its utility in the clinical field and its contribution to society are very great.

In particular, according to the IBM-BMT technology utilized in the method of the invention, not only hematopoietic stem cells but also mesenchymal stem cells can be transplanted into and maintained in a host in a good way. It is an advantage of this technology that those organs (kidney, liver, lung, etc.) damaged by an adverse effect observable upon combined use of an anticancer agent or radiotherapy can also be regenerated and/or repaired thereby.

(7) Pharmaceutical Composition

The present invention also provides a pharmacological composition for performing the above-described method for the treatment of malignant tumor. The composition comprises (a) a composition containing donor-derived PBMNCs, (b) a composition containing PBMNCs derived from the host or a third party identical in HLA type to the host and (c) a composition containing WBMCs derived from the host or a third party identical in HLA type to the host.

Each of the above compositions (a) to (c) is not particularly restricted provided that it contains the respective specified cell species to serve as an active constituent. Generally, those compositions are prepared preferably in the form suited for the route of administration thereof, for example in the form of injections, transfusions or like liquids or solutions. The liquid or solution forms, inclusive of injections, can be prepared in the same manner as in preparing various conventional pharmaceutical preparations containing cell components of this kind. The carrier to be used on that occasion may be any of various pharmaceutically acceptable carriers (diluents) so far well known in this field of art. Specific examples thereof are PBS and RPMI 1640. In preparing the above-mentioned liquid or solution forms, various technologies currently in general use in preparing various transfusions can be used. The respective compositions may be prepared just prior to use. The respective compositions are administered at respective predetermined doses via a predetermined route(s) of administration according to the method of the invention. Thus, prophylactic and curative effects on malignant tumor can be produced.

The invention further provides a pharmacological composition for carrying out the method for the prevention and treatment of DLI-induced GVHD. Said pharmacological composition comprises the compositions (b) and (c) mentioned above. The compositions (b) and (c) are administered at respective predetermined doses via a predetermined route(s) of administration, whereby the desired prophylactic and curative effects on GVHD can be produced.

EXAMPLES

The following examples illustrate the invention in further detail.

The cells utilized in each example were prepared as follows.

[Peripheral Blood Mononuclear Cells (PBMNCs)]

Donor PBMNCs and PBMNCs allogeneic to the host mouse were prepared in the conventional manner following heparinized blood collection from C57BL/6J(B6)(H-$2^b$) mice and BALB/c mice, respectively.

[Bone Marrow Cells (BMCs)]

(1) BMCs allogeneic to the host were prepared in the following manner. Thus, the femur and tibia were isolated from each BALB/c mouse allogeneic to the host, and a gage 22 needle (Code No. NN-2225RSS-02S, Terumo Co., Ltd.) attached to a syringe (2.5 ml, Code No. SS-02S, Terumo Co., Ltd.) was inserted into each of the bones from the knee joint side. Using an RPMI 1640 solution in the syringe, BMCs were flushed out into a sterilized dish (90×15 mm, Iwaki Clinical Test Wares) and then suspended in RPMI 1640 solution. The BMCs obtained were washed once with RPMI 1640 solution and then resuspended in the same solution to provide the objective bone marrow cell suspension ($1 \times 10^8$/ml concentration).

(2) Preparation, by the irrigation method, of a bone marrow cell suspension for application in humans Normal crab-eating macaques (cynomolgus monkeys, weighing 2.5-3.5 kg, intestinal parasite-free, tests for bacillary dysentery, tuberculosis, B virus, hepatitis A virus and hepatitis B virus: negative) were used as test animals. All the surgical operations and postsurgical treatments were made according to the guidelines of the National Institutes of Health for care and use of primates.

Under anesthesia with 5 mg of Ketalar (ketamine hydrochloride, Sankyo Co., Ltd.) administered intramuscularly, a bone marrow puncture needle (Katsunuma's bone marrow puncture needle (ø 1.8 mm), Kyoto, Japan) was inserted into the bone marrow of each test animal at a proximal site of the lateral condyle of the femur (in the case of the humerus, at a distal site of the greater tubercle) perpendicularly to the axis thereof, one end of an extension tube (50 cm, 3.8 ml, Code No. SF-ET3825, Terumo Co. Ltd.) was connected with the needle and the other end of the tube was placed in a culture flask (250 ml, Becton Dickinson). The flask contained 20 ml of phosphate-buffered saline (PBS) containing heparin (10 U/ml, Novo Heparin 1000, Hoechst Marion Roussel Co., Ltd.).

Another bone marrow puncture needle was inserted into the bone marrow of the test animal at a distal site of the greater trochanter of the femur (in the case of the humerus, at a proximal site of the lateral condyle) perpendicularly to the axis thereof, and connected with a syringe (30 ml, Code No. SS-30ES, Terumo Co., Ltd.) containing 30 ml of PBS. PBS was slowly extruded from the syringe into the medullary cavity to wash out the bone marrow, and the bone marrow-containing medium was recovered in the above-mentioned culture flask. The above procedure was repeated twice. The bone marrow cell suspension obtained in the above manner was layered on Mono-Poly Resolving Medium (Dainippon Pharmaceutical Co., Ltd.), centrifugation was carried out at 2000 revolutions per minute and at 15° C. for 30 minutes, and the erythrocyte sediment was removed. Thus was obtained the desired bone marrow cell suspension ($2.3 \pm 1.5 \times 10^8$ cells/ml, $2.6 \pm 1.6 \times 10^8$ cells/femur) with a reduced T cell content.

BMCs obtained were analyzed for cell surface antigens by flow cytometry (EPICS-XL, Coulter Co.) using FITC- or PE-coupled antibodies against human CD4, CD8, CD20, CD11b or CD56 (Exalpha) and IgM (Biosource) (mAbs, each preliminarily tested for the degree of cross reactivity with the molecules expressed on the cynomolgus monkey cells).

As a result, the BMCs. obtained by the above method (irrigation method) had a T cell content below 5% (CD4: 2.0±2.2%, CD8: 3.9±3.3%), whereas the BMCs obtained by the conventional aspiration method generally show a T cell content of 20% or higher (CD4$^+$ and CD8$^+$).

It is thus evident that this irrigation method gives a significantly low peripheral blood content as indicated by the frequency of appearance of CD4$^+$ and CD8$^+$ T cells.

The desired bone marrow cell suspension can be prepared from the human femur in the same manner as described above. Generally, this is administered into the bone marrow preferably at a dose of about $1 \times 10^8$ cells/kg or higher and is prepared in the form of an injection for intra-bone marrow administration containing at least such dose.

[Peripheral Blood Stem Cells (PBSCs)]

PBSCs of mouse allogeneic (identical in HLA type) to the host were collected and prepared from BALB/c mice by the method described in the above-cited documents (Blood, 15 May 2002, Vol. 99, No. 10, pp. 3838-3843; "Zoketsu Kansaibo Ishoku Manual (Hematopoietic Stem Cell Transplantation Manual)", 1st edition, 2nd printing, published Apr. 20, 1996 by Nihon-Igakukan, pages 350-367) following mobilization, as follows. Thus, on day 0, 200 mg/kg of cytosine arabinoside (AraC) was intraperitoneally administered to the mice, followed by subcutaneous administration of 250 µg/kg/day of G-CSF on day 1 to day 4. On day 5, PBMNCs were collected and suspended in PBS for use as PBMNCs (in cell suspension form).

Example 1

(1) Pretreatment of Cancer-Bearing Mice

3-Methylcholanthrene (MCA)-induced, BALB/c-derived. MethA (fibrosarcoma) cells ($5 \times 10^7$ cells) were transplanted into each BALB/c(H-$2^d$) mouse. About 2 weeks later, when a phyma or tumor having an adult little finger or larger size (but not greater than the size of an adult thumb, about 1-2 cm) was formed, the mouse was subjected to total body irradiation (TBI) at a dose of 5 Gy or lower to damage or kill and thereby destroy lymphocytes and hematopoietic system cells of the host. The above TBI was performed once using the Gamma Cell 40 Exactor (product of Nordon International Inc.) with $^{137}$Cs as the radiation source. The irradiation in the subsequent procedure was performed in the same manner except that the dose was changed.

(2) DLI

On the same day as the day of the TBI according to (1) as described above, $1 \times 10^7$ PBMNCs derived from an allogeneic C57BL/6J(B6)(H-$2^b$) mouse were transfused into the caudal vein (first DLI). This DLI procedure was repeated three times at one-week intervals.

(3) TBI

The tumor size and body weight change in the host mouse were taken as indicators, and the time when the tumor size was almost at a plateau with a body weight loss of about 2 g or more was judged as the time of onset of GVHD. At this time (3 weeks after the start of testing), TBI was performed at a dose of 3 Gy.

(4) HLI

On the same day as the day of the TBI according to (3) as described above, $1 \times 10^7$ PBMNCs derived from a BALB/c mouse allogeneic to the host were transfused into the caudal vein of the host mouse. One week later, this HLI procedure was repeated (twice in total).

(5) IBM-BMT

On the same day (within 24 hours) as the day of the HLI according to (4) described above, intra-bone marrow administration of BMCs ($3\times10^7$ cells) derived from a BALB/c mouse allogeneic to the host was performed, as follows. Thus, under pentobarbital anesthesia, the host mouse was laid in a supine position, and the area from inguinal region to knee joint was shaved and disinfected. A 5-mm-long transverse incision was made on the anterior surface of the femur at 5 mm above the superior margin of the patella, the knee joint was bent by 90-120 degrees, the proximal site of the tibia was pulled out forward, and a gage 26 needle (Terumo Co., Ltd.) was inserted thereinto at a site slightly inside the patellar tendon to thereby construct a bone opening on the tibial joint surface. The needle was further advanced by about 5 mm into the tibial bone marrow and, using a microsyringe (Hamilton Co., Ltd.) containing the host type BMCs ($3\times10^7$ cells, 0.3 ml of the suspension), the bone marrow cells were infused into the bone marrow through the above bone aperture. The skin was sutured with 5-0 nylon (Johnson and Johnson Company), and the wound region was disinfected.

(6) PBSCT

It is also possible to perform PBSCT in lieu of the above (4) and (5). This PBSCT can be performed in the same manner as the HLI described above under (4) utilizing PBSCs in lieu of PBMNCs.

(7) Test Results

Figure 2:
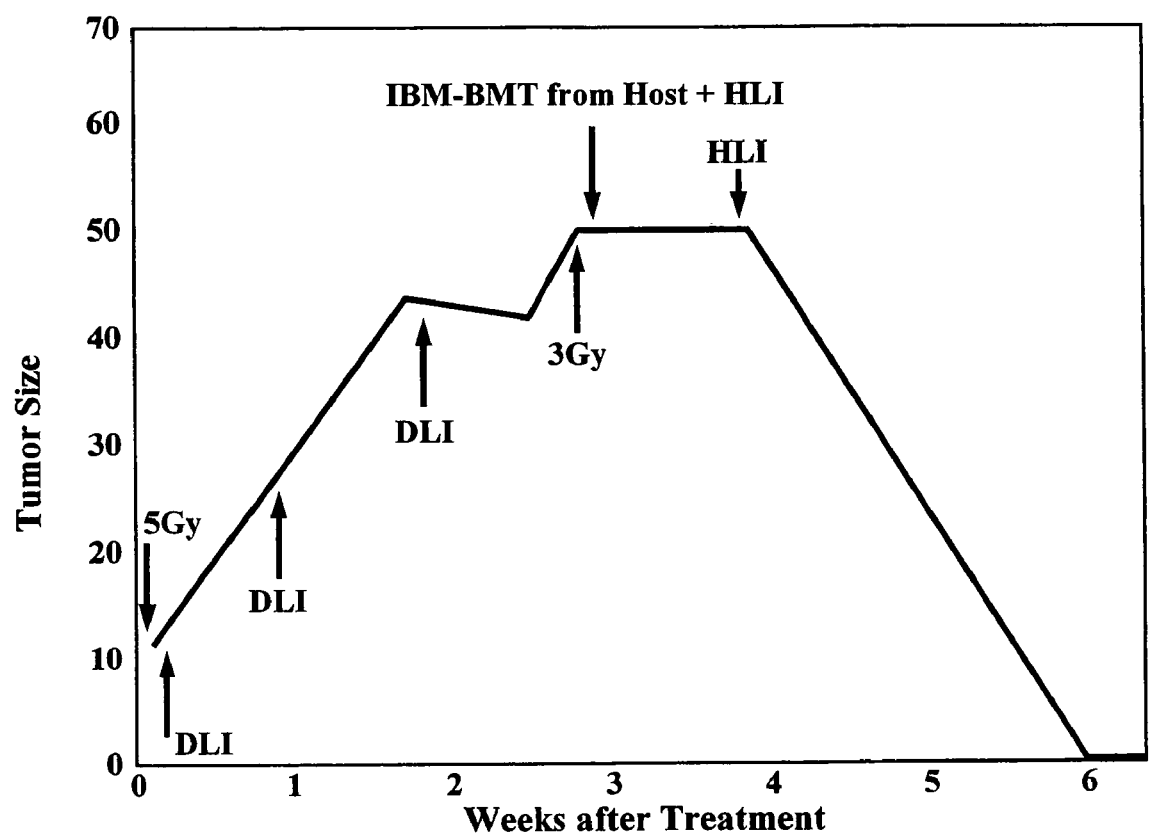
FIG. 2 is a graphic representation of the therapeutic effects on a malignant tumor (tumor size changes in test animals) as produced in accordance with the invention.

The body weights (g) and tumor sizes ($mm^3$) as measured at weekly intervals in accordance with the above administration schedule are shown in FIG. 1 (ordinate: body weight (g), abscissa: time (weeks)) and FIG. 2 (ordinate; tumor size ($mm^3$), abscissa: time (weeks)), respectively.

From the results shown in FIG. 1 and FIG. 2, it is evident that malignant tumor can be completely cured by the method of this invention while the onset of GVHD is suppressed or avoided.

The invention claimed is:

1. A method for treatment of a malignant tumor and prevention or treatment of Graft Versus Host Disease (GVHD) induced by donor lymphocyte infusion in a patient, the method comprising:
    (A) performing donor lymphocyte infusion (DLI) in a patient having a malignant tumor;
    (B) then performing:
        (i) radiation treatment (irradiation),
        (ii) infusion of lymphocytes derived from the patient or derived from a third party with an identical HLA type as the patient (HLI), and
        (iii) intra bone marrow-bone marrow transplantation (IBM-BMT) using bone marrow cells derived from the patient or derived from a third party with an identical HLA type as the patient.

2. The method of claim 1, wherein a first radiation treatment is performed prior to the donor lymphocyte infusion.

3. The method of claim 1, wherein the DLI is performed by intravenous administration of an effective amount of donor-derived peripheral blood mononuclear cells.

4. The method of claim 1, wherein said radiation treatment is performed by total body irradiation at a dose of 3-4 Gy.

5. The method of claim 1, wherein the HLI is performed by intravenous administration of an effective amount of peripheral blood mononuclear cells derived form the patient or derived from a third party with an identical HLA type as the patient.

6. The method of claim 1, wherein the bone marrow cells are whole bone marrow cells derived from the patient or derived from a third party with an identical HLA type as the patient.

7. The method of claim 6, wherein the whole bone marrow cells are obtained by inserting a bone marrow puncture needle into one end of a long bone of the patient or of the third party, causing an irrigating fluid to flow via the needle through the medullary cavity, and recovering the irrigating fluid containing bone marrow cells from a perforation provided at the other end of the long bone.

8. The method of claim 1, wherein the IBM-BMT is performed by administration, into a long bone, of an effective amount of whole bone marrow cells derived from the patient or the third party.

9. The method of claim 1, wherein the malignant tumor is selected from the group consisting of leukemia, malignant lymphoma, multiple myeloma, sarcoma, melanoma, brain tumor, stomach cancer, tongue cancer, esophageal carcinoma, colorectal cancer, liver cancer, gallbladder carcinoma, pancreatic carcinoma, renal carcinoma, bladder cancer, nasopharyngeal cancer, laryngeal cancer, skin cancer, mammary cancer, testicular cancer, ovarian cancer, uterus carcinoma, and lung cancer.

10. A method for treatment of a malignant tumor and prevention or treatment of Graft Versus Host Disease (GVHD) induced by donor lymphocyte infusion in a patient, the method comprising:
    (A) performing donor lymphocyte infusion (DLI) in a patient having a malignant tumor; and
    (B) then performing:
        (i) radiation treatment (irradiation), and
        (ii) intravenous administration of peripheral blood stem cells derived from the patient or derived from a third party with an identical HLA type to the patient.

11. A method for prevention or treatment of a graft versus host disease induced by donor lymphocyte infusion in a patient, the method comprising performing, in said patient:
    (A) radiation treatment (irradiation),
    (B) infusion of lymphocytes derived from the patient or derived from a third party with an identical HLA type as the patient, and
    (C) intra bone marrow-bone marrow transplantation using bone marrow cells derived from the patient or derived from a third party with an identical HLA type as the patient,
wherein the method prevents or treats graft versus host disease induced by donor lymphocyte infusion in the patient.

* * * * *